United States Patent
Eves et al.

(10) Patent No.: US 12,070,548 B2
(45) Date of Patent: Aug. 27, 2024

(54) PATIENT INTERFACE SYSTEMS FOR ENSURING EFFECTIVE SEAL

(71) Applicant: ResMed Pty Ltd, Bella Vista (AU)

(72) Inventors: Matthew Eves, Sydney (AU); Adam Francis Barlow, Sydney (AU); Gerard Michael Rummery, Woodford (AU)

(73) Assignee: ResMed Pty Ltd, Bella Vista (AU)

( * ) Notice: Subject to any disclaimer, the term of this patent is extended or adjusted under 35 U.S.C. 154(b) by 42 days.

(21) Appl. No.: 17/940,078

(22) Filed: Sep. 8, 2022

(65) Prior Publication Data

US 2023/0001118 A1    Jan. 5, 2023

Related U.S. Application Data

(63) Continuation of application No. 16/580,237, filed on Sep. 24, 2019, now Pat. No. 11,439,780, which is a continuation of application No. 14/214,132, filed on Mar. 14, 2014, now Pat. No. 10,456,540.

(60) Provisional application No. 61/798,900, filed on Mar. 15, 2013.

(51) Int. Cl.
*A61M 16/00* (2006.01)
*A61M 16/06* (2006.01)

(52) U.S. Cl.
CPC .... *A61M 16/0057* (2013.01); *A61M 16/0611* (2014.02); *A61M 16/0666* (2013.01); *A61M 16/0683* (2013.01)

(58) Field of Classification Search
CPC .............. A61M 16/06; A61M 16/0683; A61M 16/0666; A61M 16/0611; A61M 16/08
See application file for complete search history.

(56) References Cited

U.S. PATENT DOCUMENTS

| | | | |
|---|---|---|---|
| 6,834,650 B1 | 12/2004 | Fini et al. | |
| 7,171,966 B2 | 2/2007 | Schrader et al. | |
| 8,186,352 B2 | 5/2012 | Gunaratnam et al. | |
| 9,867,958 B2 * | 1/2018 | McCaslin | A61M 16/0622 |
| 10,456,540 B2 | 10/2019 | Eves et al. | |
| 2005/0199239 A1 | 9/2005 | Lang et al. | |
| 2006/0185675 A1 | 8/2006 | Colin | |
| 2006/0207599 A1 * | 9/2006 | Busch | A61M 16/0622 128/206.24 |
| 2007/0163594 A1 | 7/2007 | Ho | |
| 2007/0221227 A1 | 9/2007 | Ho | |
| 2008/0236588 A1 | 10/2008 | Livingston | |
| 2008/0289633 A1 | 11/2008 | Kwok | |
| 2009/0114229 A1 | 5/2009 | Frater | |
| 2010/0000534 A1 | 1/2010 | Kooij et al. | |

(Continued)

FOREIGN PATENT DOCUMENTS

| WO | WO 2004/041342 A1 | 5/2004 |
|---|---|---|
| WO | WO 2005/086943 A2 | 9/2005 |
| WO | WO 2007/068044 A1 | 6/2007 |

*Primary Examiner* — Colin W Stuart
*Assistant Examiner* — Douglas Y Sul
(74) *Attorney, Agent, or Firm* — Nixon & Vanderhye P.C.

(57) ABSTRACT

A patient interface system for delivering breathable gas to a patient includes a patient interface configured to sealingly engage the patient's face. A mechanism may be provided to ensure that an effective seal is maintained between the patient interface and the patient's face by preventing, reducing, minimizing or limiting effects of disruptive forces, such as tube drag, on the patient interface.

18 Claims, 9 Drawing Sheets

(56) References Cited

U.S. PATENT DOCUMENTS

| | | | |
|---|---|---|---|
| 2010/0083969 A1* | 4/2010 | Crumblin | A61M 16/0825 |
| | | | 285/276 |
| 2011/0088699 A1 | 4/2011 | Skipper | |
| 2012/0090617 A1* | 4/2012 | Matula, Jr. | A61M 16/0611 |
| | | | 128/206.21 |
| 2012/0157794 A1 | 6/2012 | Goodwin | |
| 2013/0133664 A1* | 5/2013 | Startare | A61M 16/0666 |
| | | | 128/206.24 |
| 2014/0261432 A1 | 9/2014 | Eves et al. | |
| 2014/0283832 A1 | 9/2014 | Stegman | |
| 2014/0366885 A1 | 12/2014 | Haibach | |
| 2015/0165152 A1* | 6/2015 | Haibach | A62B 18/084 |
| | | | 128/206.21 |
| 2015/0328422 A1* | 11/2015 | Chodkowski | A61M 16/0605 |
| | | | 128/206.21 |
| 2020/0016348 A1 | 1/2020 | Eves et al. | |

* cited by examiner

// PATENT INTERFACE SYSTEMS FOR ENSURING EFFECTIVE SEAL

CROSS REFERENCE TO APPLICATIONS

This application is a continuation of U.S. patent application Ser. No. 16/580,237, filed Sep. 24, 2019, which is a continuation of U.S. patent application Ser. No. 14/214,132, filed Mar. 14, 2014, now U.S. Pat. No. 10,456,540, which claims the benefit of U.S. Provisional Application Ser. No. 61/798,900, filed Mar. 15, 2013, each of which is hereby incorporated herein by reference in its entirety.

FIELD OF TECHNOLOGY

The present invention relates to patient interfaces and patient interface systems for delivering pressurized air to a patient (e.g., for respiratory therapy), and in particular apparatuses and methods for ensuring that an effective seal is maintained between the patient interface and the patient's face.

BACKGROUND OF TECHNOLOGY

In respiratory therapy (e.g., treatment of Sleep Disordered Breathing (SDB) such as Obstructive Sleep Apnea (OSA) with Continuous Positive Airway Pressure (CPAP) or Non-Invasive Positive Pressure Ventilation (NIPPV)) where breathable gas is delivered to a patient interface (e.g., cushion, nasal "cradle," etc.) under pressure, a good seal is typically maintained between the patient interface and the patient's face. Leaks between the patient interface and the patient's face can reduce the effectiveness of, and compliance with, the therapy, as the prescribed treatment parameters are not being maintained.

Leaks are especially prone to occur as the patient moves during the night. Movement of and drag on the air delivery tube as the patient turns or moves can alter the positioning and alignment of the patient interface with respect to the patient's face. This movement can be translated or transferred to the seal formed between the patient interface and the patient's face which may in turn create a leak in the seal. Thus, while the patient interface may initially be leak free when attached to the patient, leaks are prone to develop later in the night as the patient moves in bed which may cause the patient to waken rendering the therapy ineffective.

In certain mask designs, air pressure from within a mask chamber (or pressure chamber) may act on the underside of a mask seal, e.g., a thin flap, to urge the flap into sealing position. However in other mask designs, this air pressure effect may not impact on the seal effectiveness.

Accordingly, there is a continuous need in the art for patient interface systems, accessories, etc. that ensure a good seal between the patient interface and the patient's face is maintained.

SUMMARY OF TECHNOLOGY

A first aspect of the disclosed technology relates to a patient interface system configured to prevent or reduce deleterious effects of disruptive forces (e.g., tube drag) on the seal between a patient interface and the patient's face.

Another aspect of the disclosed technology relates to an apparatus arranged to maintain a patient interface in sealing relation with a patient's face.

Another aspect of the disclosed technology relates to an apparatus configured to prevent, limit, minimize or reduce degradation of a seal between a patient interface and a patient's face.

Another aspect of the disclosed technology relates to an apparatus configured to absorb disruptive forces (e.g., tube drag) exerted on a patient interface.

Another aspect of the disclosed technology is a method and apparatus to improve the robustness and/or effectiveness of a seal between a patient interface and a patient's face when an air pressure effect acting on the underside of a seal portion of the patient interface does not provide an adequate seal with the patient's face.

Another aspect of the disclosed technology is a patient interface having a pressure chamber, and seal portion that is not supported by air pressure in use.

Another aspect of the disclosed technology is a patient interface having a seal member with an interior surface and an exterior surface, and wherein a seal is formed in use with a portion of the interior surface of the seal member.

Another aspect of the disclosed technology relates to an apparatus for ensuring an effective seal is maintained between a respiratory patient interface and a patient's face, the respiratory patient interface adapted to receive pressurized gas from a supply tube and deliver the pressurized gas to the patient's airways, the patient interface including a seal portion adapted to seal against the patient's face. The apparatus comprises a device having a lower portion operatively coupled to the supply tube and an upper portion disposed adjacent the seal portion of the patient interface, wherein movement of the supply tube causes the device to urge the seal portion of the patient interface toward the patient's face.

Another aspect of the disclosed technology relates to an apparatus for preventing leakage between a respiratory patient interface and a patient's face, where the respiratory patient interface is adapted to receive pressurized gas from a supply tube and deliver the pressurized gas to the patient's airways, and the patient interface includes left and right portions adapted to seal against the patient's face. The apparatus comprises first and second arms pivotally coupled to one another. The first and second arms each include lower portions coupled to the supply tube and upper portions disposed respectively adjacent the left and right portions of the patient interface, wherein movement of the supply tube causes the first and second arms to urge the left and right portions of the patient interface toward the patient's face.

Another aspect of the disclosed technology relates to a patient interface system for delivering pressurized gas to a patient's airways. The system comprises a supply tube to deliver a supply of pressurized gas; a patient interface to receive the supply of pressurized gas from the supply tube and deliver the pressurized gas to the patient's airways, the patient interface including left and right portions adapted to seal against the patient's face; and a scissor mechanism including first and second arms pivotally coupled to one another, the first and second arms each including lower portions coupled to the supply tube and upper portions disposed respectively adjacent the left and right portions of the patient interface, wherein movement of the supply tube causes the first and second arms to urge the left and right portions of the patient interface toward the patient's face.

Another aspect of the disclosed technology relates to a patient interface system for delivering pressurized gas to a patient. The system comprises a patient interface adapted to sealingly communicate with the patient's nose; and a support pad connected to the patient interface to at least partially support the patient interface on the patient's face, the support pad structured to rest on a nasal bridge region of the patient's face, wherein the support pad is secured to the patient by at least one first strap having a vector with a downward directional component or an adhesive that requires no straps.

Another aspect of the disclosed technology relates to a patient interface for delivering pressurized gas to a patient. The patient interface comprises a patient contacting side adapted to sealingly engage the patient's face by a compressive force; a non-patient contacting side opposite the patient contacting side; and a chamber extending from a seal-side portion on the patient contacting side to a non-seal side portion on the non-patient contacting side, the chamber including a fluid, wherein the fluid flows between the seal-side portion of the chamber and the non-seal side portion of the chamber in accordance with a magnitude of the compressive force.

Another aspect of the disclosed technology relates to a patient interface for delivering pressurized gas to a patient. The patient interface comprises a patient contacting side adapted to sealingly engage the patient's face by a compressive force; a non-patient contacting side opposite the patient contacting side; and a chamber extending from a seal-side portion on the patient contacting side to a non-seal side portion on the non-patient contacting side, the chamber including a fluid, wherein the seal-side portion includes an inner elastic wall and an outer wall, and the inner wall elastically expands as fluid flows from the non-seal side portion to the seal-side portion.

Another aspect of the disclosed technology relates to a method of sealing a patient interface with a patient's face, the patient interface configured to deliver pressurized gas to the patient, the patient interface comprising a patient contacting side adapted to sealingly engage the patient's face, a non-patient contacting side opposite the patient contacting side, and a fluid-filled chamber extending from a seal-side portion on the patient contacting side to a non-seal side portion on the non-patient contacting side. The method comprises engaging the patient contacting side of the patient interface with the patient's face thereby applying a compressive force to the patient interface; forming at least a partial seal between the patient interface and the patient's face; and expanding the seal-side portion of the chamber by causing fluid to flow from the non-seal side portion to the seal-side portion of the chamber in response to a decrease in the compressive force.

Another aspect of the disclosed technology relates to a patient interface system for delivering pressurized gas to a patient. The system comprises a patient interface adapted to seal against the patient's face; a frame element to at least partially support the patient interface on the patient's face; and at least one resilient member disposed between the patient interface and the frame element to urge the patient interface against the patient's face.

Another aspect of the disclosed technology relates to a patient interface system for delivering pressurized gas to a patient. The system comprises a patient interface including first and second side portions adapted to seal against the patient's face; and at least one resilient member coupled to the patient interface and configured to absorb a disruptive force thereby preventing degradation of the seal against the patient's face.

Another aspect of the disclosed technology relates to a patient interface system for delivering pressurized gas to a patient. The system comprises a patient interface including a seal portion configured to sealingly engage the patient's face; and a device coupled to the seal portion and arranged to exert a force against the seal portion to urge the seal portion against the patient's face in response to a disruptive force exerted on the seal portion.

Still another aspect of the disclosed technology relates to a patient interface system for delivering pressurized gas to a patient. The system comprises a patient interface including seal means configured for sealingly engaging the patient's face; and seal maintaining means for exerting a force against the seal means to urge the seal means against the patient's face in response to a disruptive force exerted on the seal means.

Other aspects, features, and advantages of this technology will become apparent from the following detailed description when taken in conjunction with the accompanying drawings, which are a part of this disclosure and which illustrate, by way of example, principles of this invention.

BRIEF DESCRIPTION OF THE DRAWINGS

The accompanying drawings facilitate an understanding of the various embodiments of this technology. In such drawings:

FIGS. 1-1 and 1-2 are schematic representations of a patient interface system according to an example of the disclosed technology;

FIG. 2-1 is a perspective view of a patient interface system according to another example of the disclosed technology;

FIG. 2-2 is a front view of the patient interface system of FIG. 2-1;

FIG. 2-3 is a side view of the patient interface system of FIG. 2-1;

FIG. 3-1 is a perspective view of patient interface according to another example of the disclosed technology;

FIG. 3-2 is a side view of the patient interface of FIG. 3-1;

FIG. 3-3 is a cross-sectional view along the line 3-3—3-3 in FIG. 3-2;

FIG. 3-4 is a cross-sectional view of the patient interface of FIG. 3-1 showing movement of fluid from a non-seal side portion to a seal-side portion of the chamber;

FIG. 4-1 is a front perspective view of a patient interface system according to another example of the disclosed technology;

FIG. 4-2 is a schematic representation of the patient interface system of FIG. 4-1;

FIG. 4-3 is a schematic representation of the patient interface system of FIG. 4-1 in response to a disruptive force against the patient interface system;

FIG. 5-1 is a front perspective view of a patient interface system according to another example of the disclosed technology;

FIG. 5-2 is a schematic representation of the patient interface system of FIG. 5-1; and FIG. 5-3 is a schematic representation of the patient interface system of FIG. 5-1 in response to a disruptive force against the patient interface system.

DETAILED DESCRIPTION OF ILLUSTRATED EXAMPLES

The following description is provided in relation to several examples which may share common characteristics and features. It is to be understood that one or more features of any one example may be combinable with one or more features of the other examples. In addition, any single feature or combination of features in any of the examples may constitute an additional example or examples.

In this specification, the word "comprising" is to be understood in its "open" sense, that is, in the sense of "including", and thus not limited to its "closed" sense, that is the sense of "consisting only of". A corresponding meaning is to be attributed to the corresponding words "comprise", "comprised" and "comprises" where they appear.

1. Patient Interface Systems

In treatment of SDB (e.g., by pneumatically splinting the patient's airways with gas or air pressurized in the range of about 2-30 cm $H_2O$ (typically 8-12 cm $H_2O$)), a variety of patient interfaces may be used to deliver the breathable gas to the patient's airways. As an example, suitable patient interfaces may include nasal and/or oral cushions, nasal "cradles," nasal "pillows," nasal prongs, nozzles, and cannulae. An interior area of the patient interface defined by the seal between the patient and the patient interface may be considered a pressure chamber. As mentioned above, to ensure effective therapy, a good seal between the patient interface and the patient should be maintained.

Thus, the patient interface system should be designed to avoid leakage that causes annoyance and/or discomfort to the patient and to improve the quality of the therapy by reducing or eliminating problems associated with leakage.

As the patient moves during the night, disruptive forces such as tube drag are transferred to the patient interface tending to cause the positioning of the patient interface to become altered, thereby increasing the likelihood that the seal will leak. Patient interface systems according to examples of the disclosed technology may be designed with various seal maintenance structures (described below) to prevent, reduce or stop such leakage from the patient interface. The patient interface systems may also be designed to reduce or eliminate noise disturbance to the patient, which may be a consequence of a leaking seal.

It is noted that features described herein for preventing or reducing leakage described in relation to a particular patient interface may also be useable with a different patient interface.

2. Scissor Mechanism

Figure 11:
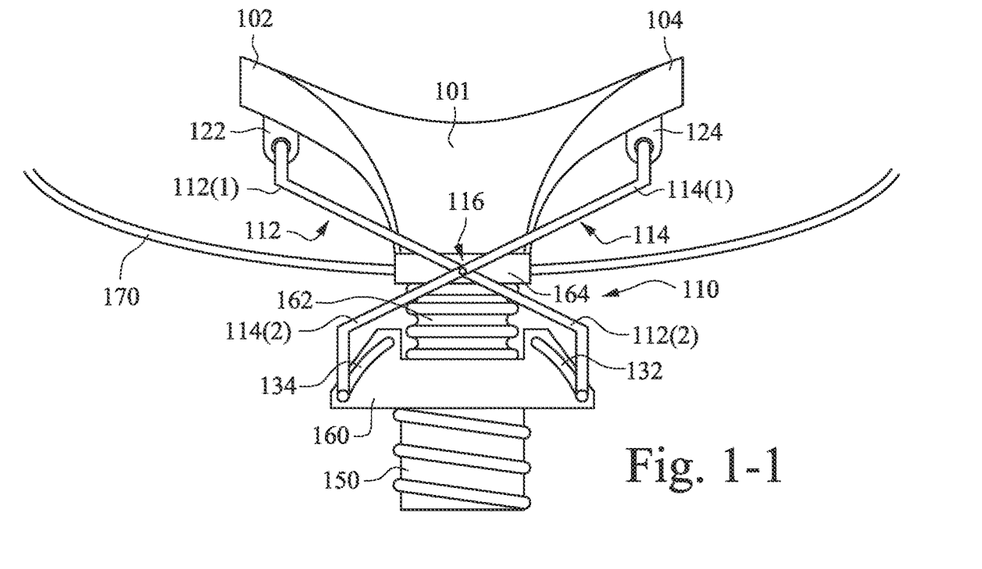
Figure 12:
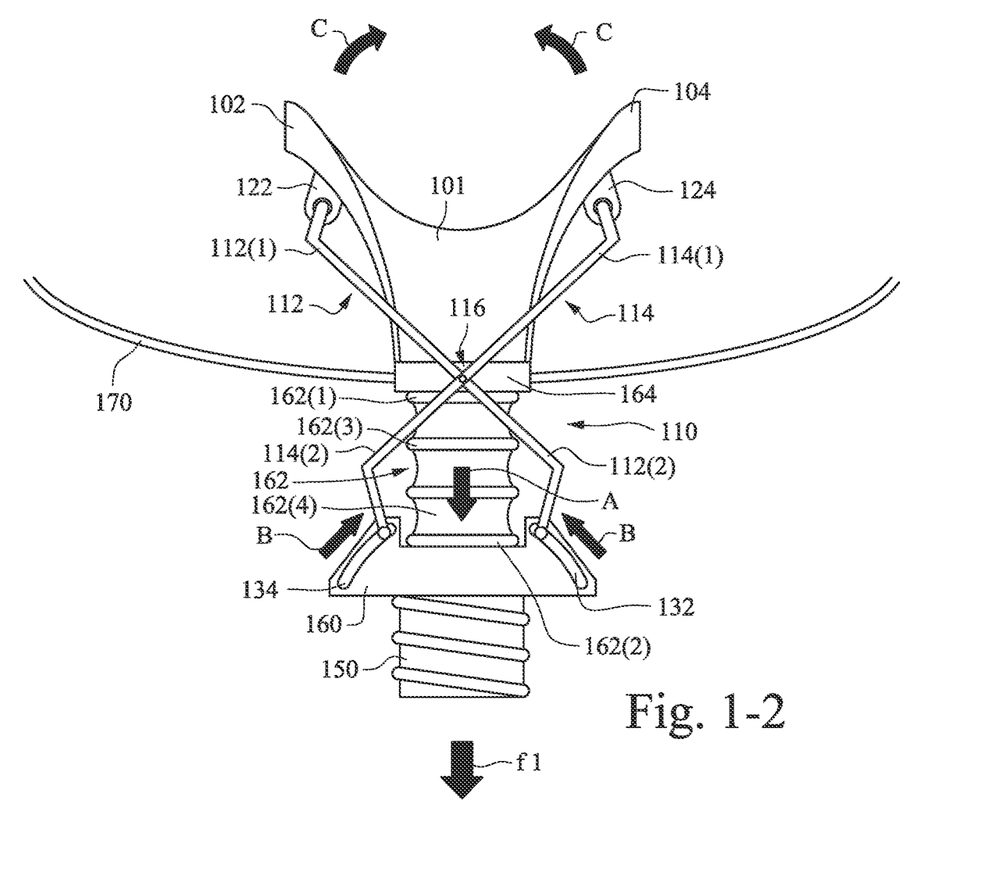

Referring to FIG. 1, a patient interface system includes a nasal cradle 101 and a seal maintenance device 110 to prevent movement of a supply tube 150 from disrupting the seal with the patient's face. The nasal cradle 101 is placed at an entrance to the patient's nares, resting on an upper lip region of the patient's face. The nasal cradle is structured to form an interface with the nares and includes right and left 102, 104 portions (seal portions) (from the patient's perspective when the patient interface worn) that seal with the sides of the patient's nose, or the external nares. The supply tube 150 is coupled to the nasal cradle 101 and is arranged to deliver breathable gas to the patient. Headgear 170 may aid is supporting the cradle 101 on the patient's face.

The seal maintenance device 110 includes an actuator 160 coupled to the supply tube 150, an extensible connector 162 connecting the actuator 160 and the cradle 101, first and second scissor arms 112, 114 having respective upper portions 112(1), 114(1) coupled to the cradle 101 and respective lower portions 112(2), 114(2) coupled to the actuator 160, and a support member 164 for pivotably supporting the first and second scissor arms 112, 114. The seal maintenance device 110 may be coupled to the supply tube 150 such that a downward (or any other direction tending to pull the tube away from the patient's face) force (e.g., caused by tube drag) on the tube 150 is transferred to the seal maintenance device 110 to prevent the force from causing leakage at the seal.

The support member 164 is connected to or otherwise anchored by the headgear 170. In an example, the support member 164 may form part of the headgear 170. The extensible connector 162 has a first end 162(1) connected to the support member 164 and a second end 162(2) connected to the actuator 160. When a disruptive force f1 is applied to the supply tube 150, the actuator exerts a force on the second end 162(2) of the extensible connector 162. As a result, the extensible connector 162 extends its length in the direction of arrow A due to its extensible construction and the connection of the first end 162(1) to the support member 164. That is, the first end 162(1) of the extensible connector 162 is anchored via its connection to the support member 164 which is in turn connected to headgear 170 which is securely fastened to the patient's head. The pivot 116 of the scissor arms 112, 114 is also connected to the support member 164. The support member 164 may be formed of a substantially rigid material (e.g., metal, hard plastic, etc.).

The extensible connector 162 is constructed in a manner that allows it to extend its length so as to be movable from a compressed positioned to an extended position. Such movement of the extensible connector 162 effectively decouples movement of the supply tube 150 from the cradle 101. As such, transference of the force f1 to the cradle 101 is minimized or even completely eliminated. In the illustrated example, the extensible connector 162 will retract to the compressed position, shown in FIG. 1-1, when no external force is applied which would cause the extensible connector 162 to extend. In an example, the extensible connector 162 may include rigid portions 162(3) and flexible portions 162(4) such that the flexible portions may tend to fold when the extensible connector 162 is compressed and stretch out when the extensible connector is extended.

The actuator 160 is connected to the second end 162(2) of the extensible connector 162. Thus, when the disruptive force f1 is applied, the actuator 160 moves away from the cradle 101 along with the supply tube 150 and the extensible connector 162. The actuator may include a pair of slots 132, 134 formed therein and configured to respectively receive the lower portions 112(2), 114(2) of the first and second scissor arms 112, 114. The slots 132, 134 may be curved or angled such that proximal ends of the slots (with respect to the patient) are disposed inwardly of distal ends of the slots. As such, movement of the actuator 160 away from the patient will cause the lower portions 112(2), 114(2) of the scissor arms to move closer (inwardly) to one another, in the direction of arrows B. Such inward movement of the lower portions 112(2), 114(2) of the scissor arms 112, 114 causes the upper portions 112(1), 114(1) of the scissor arms to swing towards one another. This motion causes the upper portions 112(1), 114(1) to exert a force on the right and left portions 102, 104 of the nasal cradle 101 to urge the right and left portions 102, 104 against the patient's face, in the direction of arrows C. The upper portions 112(1), 114(1) of the scissor arms may cause the right and left portions 102, 104 of the cradle 101 to stretch lengthwise as well as move inwardly, as shown by the direction of the arrows C. By converting motion of the supply tube 150 away from the patient's face into motion of the seal maintenance device 110 which actually urges the nasal cradle 101 towards the patient's face, deleterious effects of tube drag and other disruptive forces can be overcome and a good seal can be maintained as the patient moves during the night.

The upper portions 112(1), 114(1) may be respectively pivotably connected (e.g., via connectors 122, 124) to the right and left portions 102, 104 of the cradle 101. Connectors 122, 124 may be attached to the cradle and include a portion pivotably connected to the upper portions 112(1), 114(1) of the scissor arms. Such pivotal connection may be about a single axis, two axes, or more than two axes (e.g., a ball and socket joint).

The actuator 160 may provide a swivel connection to the supply tube 150. The first and second scissor arms 112, 114 may be constructed of a rigid or semi-rigid material such as nylon, polypropylene, polycarbonate, or silicone having a Shore A hardness with the range of 30-90, preferably 40-70, for example. The actuator 160 may be formed of a substantially rigid material (e.g., metal, hard plastic, etc.)

3. Support Pad

Figure 21:
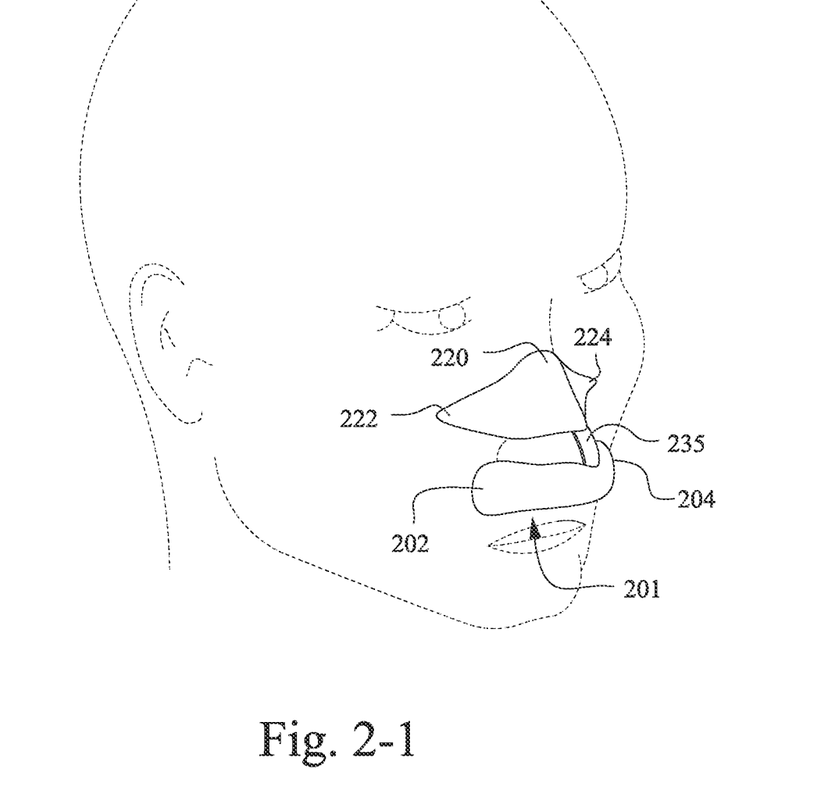
Figure 22:
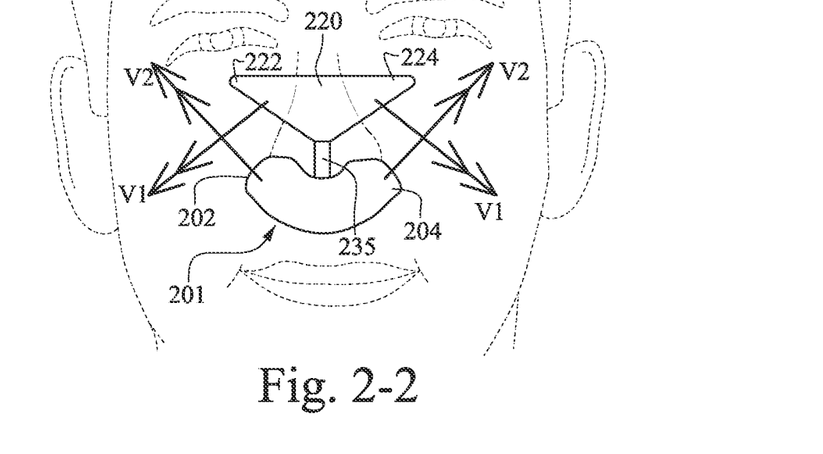
Figure 23:
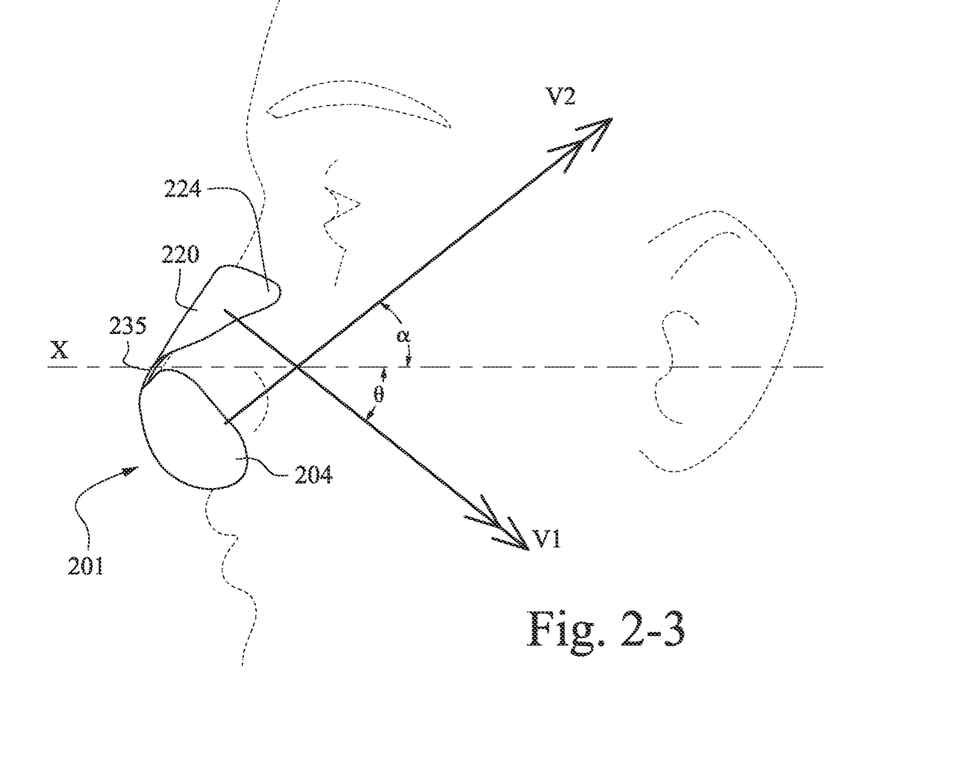

Referring to FIGS. 2-1 to 2-3, a patient interface system includes a nasal cradle 201 and a support pad 220 to help stabilize the cradle and to prevent movement of a supply tube from disrupting the seal with the patient's face. Similar to the nasal cradle 101 described above, the nasal cradle 201 is placed at an entrance to the patient's nares, resting on an upper lip region of the patient's face. The nasal cradle is structured to form an interface with the nares and includes right and left 202, 204 portions (seal portions) that seal with the sides of the patient's nose, or the external nares. A supply tube (not shown) connects to the nasal cradle 201 to provide a supply of gas.

A connecting member 235 extends over the tip of nose region and interconnects the nasal cradle 201 and the support pad 220 which is positioned generally over the nasal bridge region of the patient's face. The support pad 220 and/or the connecting member 235 may be made from a rigid material, a flexible material, or a combination of rigid and flexible materials. Suitable materials for the support pad and connecting member may include a silicone, polyurethane, adhesive backed cotton or textile. The support pad 220 and/or the connecting member 235 may have a relatively high friction coefficient to limit downwards movement along the patient's nose.

Upper straps may be connected to the right and left portions 202, 204 of the nasal cradle to support the nasal cradle 201, particularly the top of lip and under the nose region of the cradle. The upper straps extend upwardly at an angle α within the range of 30-60°, preferably 45°, with respect to the horizontal axis X. V1 represents vectors for the upper straps and indicates the direction of force applied to the nasal cradle by the straps. The upper straps may enhance the seal at the sides of the patient's nose by pulling the nasal cradle 201 into close conformance with the curvature of the patient's nose.

Lower straps may be connected to the right and left portions 202, 204 of the support pad 220 to stabilize the tip of nose region of the cradle 201, particularly when a disruptive force such as tube drag is transferred to the cradle. The lower straps extend downwardly at an angle θ within the range of 30-60°, preferably 45°, with respect to the horizontal axis X. V2 represent vectors for the lower straps and indicates the direction of force applied to the support pad 220 by the straps.

The support pad 220 and system of upper and lower straps function to support and stabilize the nasal cradle 201 such that in the event of a disruptive force, such as tube drag, the nasal cradle may be securely held against the patient's face to prevent or minimize leakage at the seal.

In another example, instead of the nasal cradle 201, a different patient interface may be used, e.g., a pair of nasal pillows, such that the connecting member 235 extends over the tip of nose region and interconnects the nasal pillows and the support pad 220.

4. Fluid Chamber

Referring now to FIGS. 3-1 to 3-4, a cushion 300 is shown. In the illustrated example, the cushion 300 is a nasal cushion configured to engage the patient's nose, although other cushion types may be used. The cushion 300 includes a non-face-contacting side 312 and a face-contacting side 314. The non-face-contacting side 312 is connected to a connecting member 305 which provides a supply of breathable gas to the cushion 300. The connecting member 305 may be a supply tube, a connector (such as a swivel connector or ball and socket type connector) interconnecting the cushion and a supply tube, or any other appropriate mechanism to introduce the breathable gas to the cushion. The breathable gas is communicated to the patient by an aperture 319 via a channel 321 extending through the cushion 300. Suitable materials for the cushion 300 include Silicone, polyurethane, rubber and textiles.

Figure 31:
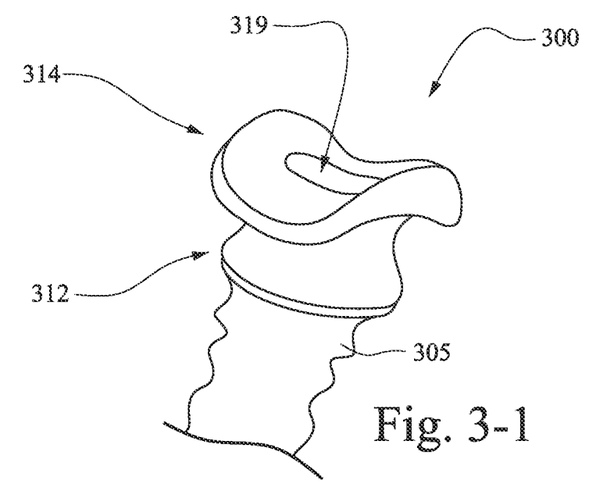
Figure 32:
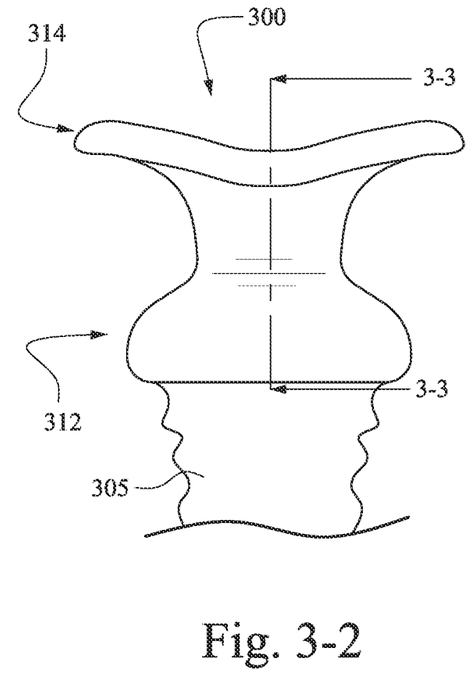
Figure 33:
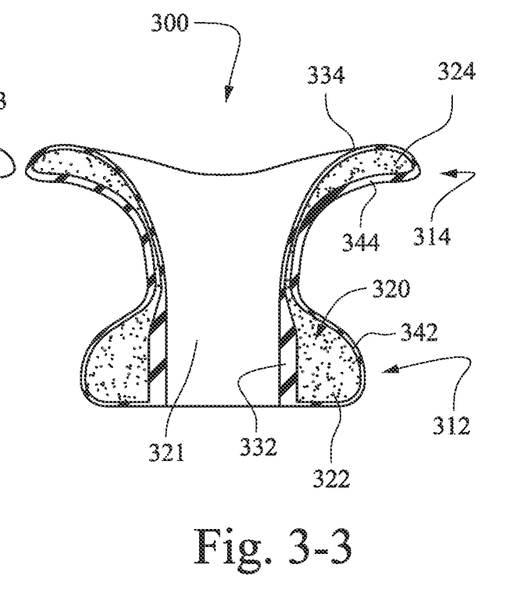

The cushion 300 includes a compressible interior fluid chamber and thus forms a compression or gasket-type seal with the patient's face. The chamber 320 may be filled with any fluid (e.g., gas, liquid) or gel as long as they are flowable. The cushion 300 relies on its softness and compliance, through compression of the fluid chamber 320, in a direction normal to the patient's face to conform to the patient's facial anatomy.

As shown in FIG. 3-3, the fluid chamber 320 extends from the non-face-contacting side 312 to the face-contacting side 314 of the cushion. The chamber 320 has a non-seal side portion 322 on the non-face-contacting side 312 of the cushion and a seal-side portion 324 on the face-contacting side 314 of the cushion. The aperture 319 is delimited by an inner wall having a first (lower) inner wall portion 332 on the non-face-contacting side 312 of the cushion and a second (upper) inner wall portion 334 on the face-contacting side 314 of the cushion. The inner wall is joined to an outer wall having a first (lower) outer wall portion 342 on the non-face-contacting side 312 of the cushion and a second (upper) outer wall portion 344 on the face-contacting side 314 of the cushion. The face-contacting side 314 (e.g., second inner wall portion 334) of the cushion forms a seal portion that seals with the patient's face (e.g., nose, e.g., sides of the patient's nose, or the external nares).

The second inner wall portion 334 is relatively thin as compared to the first inner wall portion 332 which has a thicker cross-section. The thinner arrangement of the second inner wall portion 334 allows for better conformance to the patient's face. This arrangement also allows the second inner wall portion 334 to elastically expand and contract as fluid (or gel) in the chamber 320 flows to and from the seal-side portion 324 of the chamber 320.

The first outer wall portion 342 is relatively thin as compared to the second outer wall portion 344 which has a thicker cross-section. The second outer wall portion 344 forms an outer wall of the seal-side portion 324 of the chamber 320. The thicker second outer wall portion 344 resists distortion and forms a stable base which allows the thinner second inner wall portion 334 to expand and contract when fluid flows to and from the seal-side portion 324 of the chamber. That is, the second inner wall portion 334 is thinner than the second outer wall portion 344 to encourage the second inner wall portion 334 to expand and conform to the patient's face to create an effective seal as the fluid or gel flows into the seal-side portion 324 of the chamber 320.

Similarly, the thicker first inner wall portion 332 resists distortion and forms a stable base which allows the thinner first outer wall portion 342 to elastically expand and contract when fluid flows to and from the non-seal side portion 322 of the chamber 320. More specifically, occlusion of the channel 321 is prevented by the thicker first inner wall portion 332 which resists distortion and expansion as the fluid or gel flows into the non-seal side portion 322 of the chamber 320.

Figure 34:
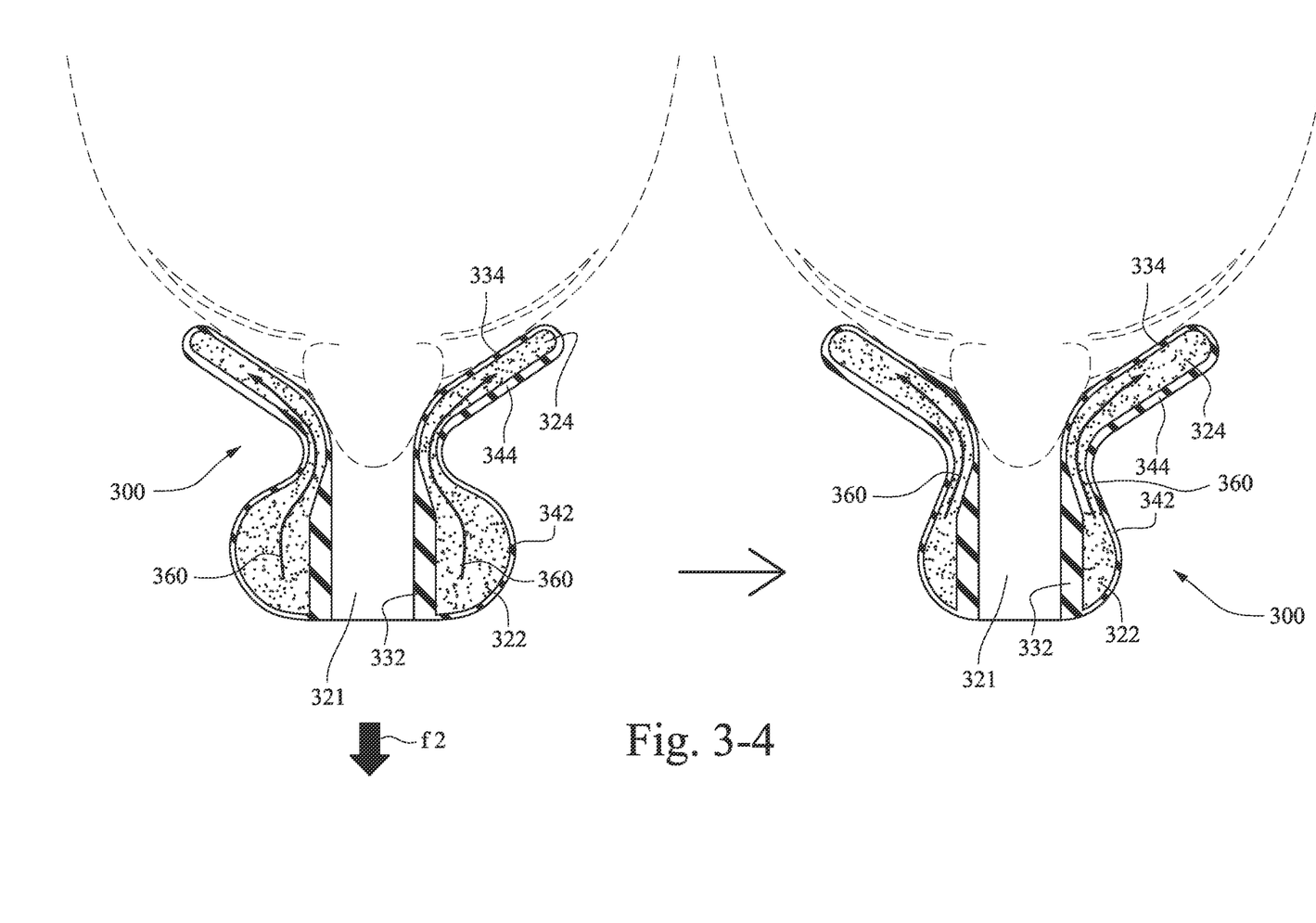

In use, as the patient's face is pressed against the face-contacting side 314 of the cushion 300 (e.g., as a result of headgear holding the cushion against the patient's face), the seal-side portion 324 of the chamber compresses and the second inner wall portion 334 conforms to the patient's face to form a seal therewith. Compression of the seal-side portion 324 of the chamber 320 causes the fluid or gel to shift toward the non-seal side portion 322 of the chamber. Fluid flow into the non-seal side portion 322 causes the first outer wall 342 to expand elastically. If, for example, the force applied by the headgear is reduced, or a disruptive force such as tube drag displaces the cushion, the first outer wall portion 342 will contract to force fluid in the direction of arrows 360 toward the seal-side portion 324 of the chamber. As a result, the seal-side portion 324 expands (via elastic expansion of the second inner wall portion 334), increasing the thickness or height of the face-contacting side 314 of the cushion to fill any gap (between the patient's face and the cushion) caused by the displacement, as shown in FIG. 3-4.

5. Spring Support

Figure 41:
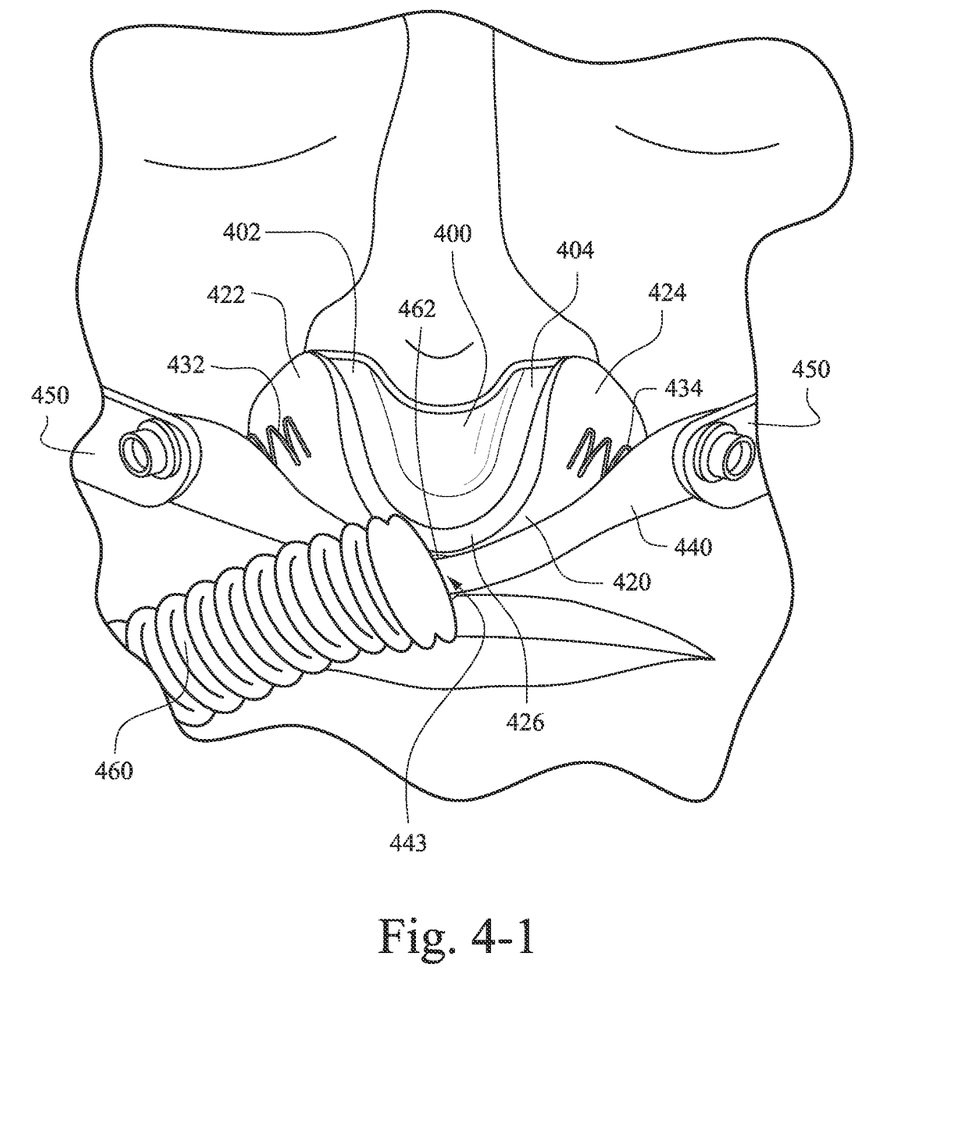
Figure 42:
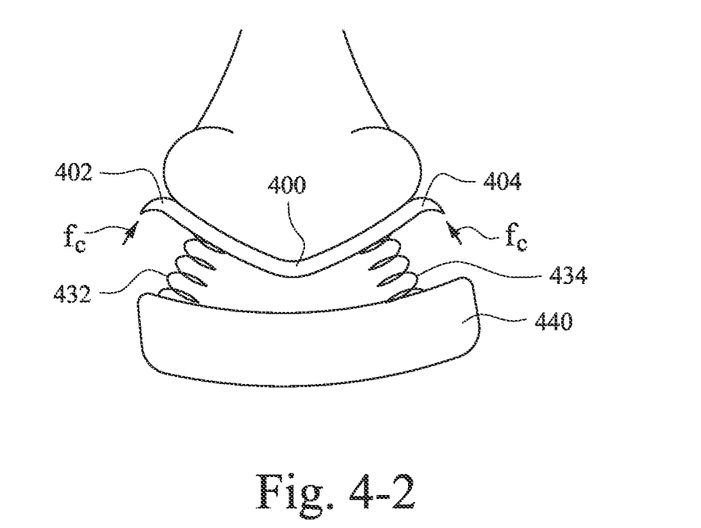
Figure 43:
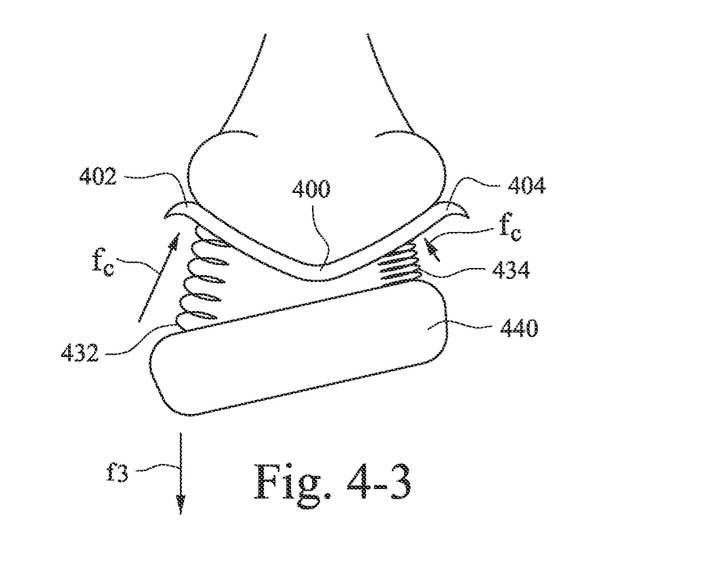
Figure 51:
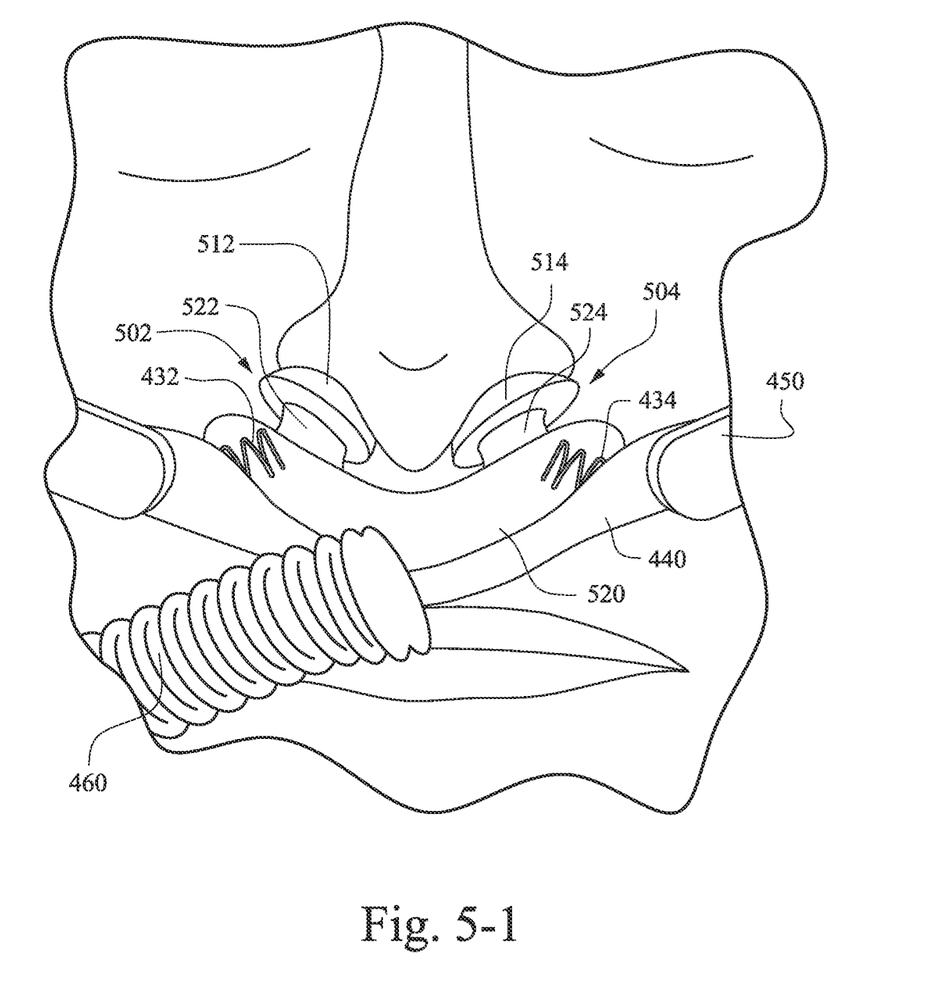
Figure 52:
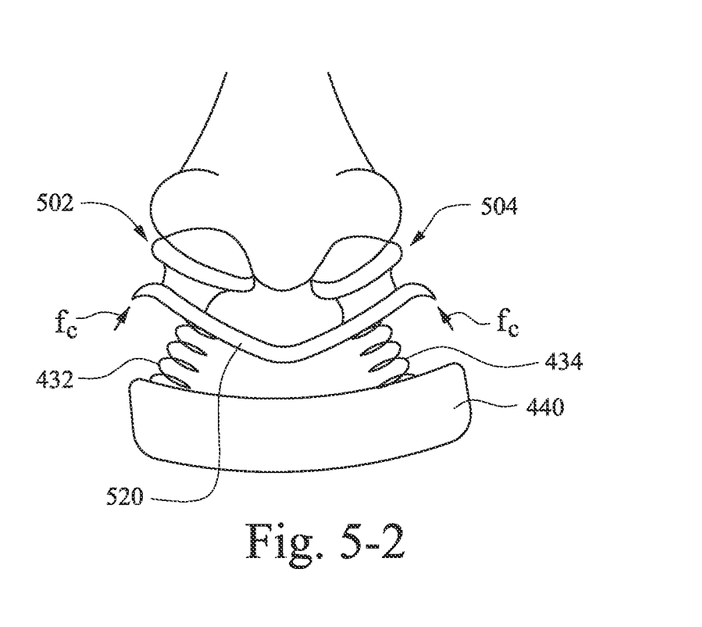
Figure 53:
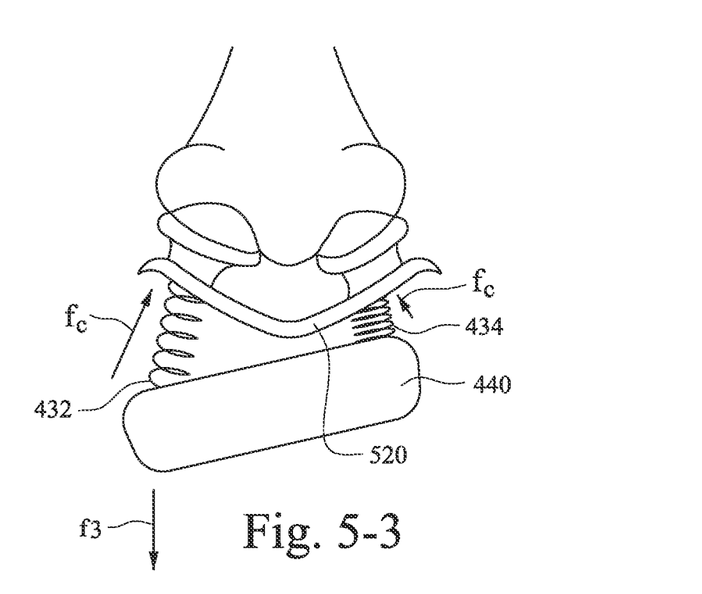

FIGS. 4-1 to 4-3 show a patient interface system including a nasal cradle 400 and a resilient member to support the nasal cradle in sealing engagement with the patient's face. The nasal cradle 400 is structured to form an interface with the nares and includes right and left portions 402, 404 (seal portions) that seal with the sides of the patient's nose, or the external nares. The resilient member may be arranged to passively counteract disruptive forces (e.g., tube drag) and thereby maintain an effective seal. That is, the resilient member may be configured to absorb a disruptive force thereby preventing degradation of the seal against the patient's face. Additionally, or alternatively, the resilient member may be configured to urge the seal portion against the patient's face in response to a disruptive force exerted on the seal portion.

The resilient member may comprise one or more springs, such as a mechanical spring. In another example, the resilient member may be a flexible beam, e.g., that is configured to bend. The resilient member may also be a compressible member. The resilient member may be constructed from an elastomeric material. The resilient member may be constructed from a foam, e.g., an elastic foam, and/or a viscoelastic foam. In the illustrated example, the patient interface system includes springs 432, 434.

In an example, the patient interface system may include an optional bow-shaped elastic member 420 which extends around the cradle 400 and includes right and left sides 422, 424 connected respectively to the right and left portions 402, 404 of the cradle. A supply tube 460 is connected to the frame 440 and is in fluid communication with an inlet 462 of the elastic member 420 or the cradle 400 to provide breathable gas to the patient's airways via the nasal cradle. A middle portion 426 of the elastic member 420 or the cradle 400 is connected to a frame at an engaging portion 443 of the frame. The middle portion 426 may be seated in the frame 440, which may have a concave shape, or otherwise engaged with the frame which provides a rigid support for the nasal cradle 400 and/or the elastic member 420. The frame 440 is connected to headgear 450 at its ends.

As mentioned above, the elastic member 420 may be omitted and the springs 432, 434 may be connected directly to the right and left portions 402, 404 of the nasal cradle 400.

The spring 432, (e.g., a compression spring), is disposed between the right side 422 of the elastic member (or right and left portions of the nasal cradle) and a corresponding portion of the frame 440. Likewise, the spring 434 is disposed between the left side 424 of the elastic member and a corresponding portion of the frame. The springs 432, 434 are compressed when the nasal cradle 400 is positioned on the patient's face. As such, the springs exert outward forces $f_c$ against both the frame 440 and the right and left 422, 424 sides of the elastic member 420 (or the right and left portions 402, 404 of the nasal cradle 400 if connected directly thereto). Since the frame is a sturdy, rigid or semi-rigid member, the springs 432, 434 tend to push the right and left 402, 404 portions of the nasal cradle against the patient's nose which aids in establishing a good seal.

In use, springs 432, 434 are in compression. Thus, if a disruptive force f3 such as tube drag acts to pull the frame 440, the elastic member 420, or the cradle 400 away from the patient's nose, the springs 432, 434 will resist such movement of the elastic member 420 or nasal cradle 400, thus effectively decoupling the cradle 400 from the frame 440 and the supply tube 460, as shown in FIGS. 4-2 and 4-3. In response to the disruptive force f3, the springs may extend, for example as shown with regard to spring 432 in FIG. 4-3. Although the spring 432 extends (is partially unloaded) in response to the disruptive force f3, the spring 432 remains in compression. Therefore, spring 432 continues to exert force $f_c$ against the right portion 402 of the nasal cradle. In the illustrated example, since disruptive force f3 is exerted on the right side of the nasal cradle, while spring 432 is partially unloaded, spring 434 may be further loaded thereby also remaining in compression. As such, the patient interface system may exhibit an increased ability to overcome such disruptive forces and prevent or limit degradation of the seal since the springs 432, 434 remain in compression at all times thereby ensuring an outward force $f_c$ by the springs pushes the nasal cradle towards the patient's face to maintain a good seal even when a disruptive force is exerted on the patient interface.

Springs 432, 434 may be formed of resilient metals (e.g., spring steel). Springs 432, 434 may also be formed of a resilient thermoplastic material.

In another example, an air pocket is disposed between the frame 440 and the nasal cradle in place of the springs 432, 434. The air pocket would resist compression and therefore in the event of a disruptive force such as tube drag, would exert a force tending to push the nasal cradle against the patient's nose. Other materials, such as silicone, metal, plastic and gel may be used to function as a spring.

It is also noted that the springs may be disposed at different locations along the nasal cradle to stabilize the seal in that region (e.g., nose tip region).

Further, instead of the nasal cradle 400, a different patient interface may be used, e.g., a pair of nasal pillows, such that the springs 432, 434 are positioned between a frame member and the nasal pillows to urge the nasal pillows into sealing engagement with the patient's nares, as shown in FIGS. 5-1 to 5-3. Referring to FIG. 5-1, springs 432, 434 may be disposed between the frame 440 and a support member 520 which supports a pair of nasal pillows 502, 504. The nasal pillows each include a conical portion 512, 514 (seal portions) supported by a respective stem portion 522, 524. Each of the conical portions 512, 514 includes a surface that seals against surfaces of the patient's nose surrounding the nares. Springs 432, 434 function in the manner described above in relation to FIGS. 4-1 to 4-3 to maintain the nasal pillows 502, 504 in sealing engagement with the patient's face even when a disruptive force is exerted on the patient interface.

While the technology has been described in connection with several examples, it is to be understood that the technology is not to be limited to the disclosed examples, but on the contrary, is intended to cover various modifications and equivalent arrangements included within the spirit and scope of the technology. Also, the various examples described above may be implemented in conjunction with other examples, e.g., one or more aspects of one example may be combined with one or more aspects of another example to realize yet other examples. Further, each independent feature or component of any given assembly may constitute an additional example. In addition, while the technology has particular application to patients who suffer from OSA, it is to be appreciated that patients who suffer from other illnesses (e.g., congestive heart failure, diabetes, morbid obesity, stroke, bariatric surgery, etc.) can derive benefit from the above teachings. Moreover, the above teachings have applicability with patients and non-patients alike in non-medical applications.

PARTS LIST

101 Nasal cradle
102 Right portion of nasal cradle
104 Left portion of nasal cradle
110 Seal maintenance device
112 First scissor arm
112(1) Upper portion
112(2) Lower portion
114 Second scissor arm
114(1) Upper portion
114(2) Lower portion
116 Pivot
122 Connector
124 Connector
132 Slot
134 Slot
150 Supply tube
160 Actuator
162 Extensible connector
162(1) First end of extensible connector
162(2) Second end of extensible connector
162(3) Rigid portions
162(4) Flexible portions
164 Support member
170 Headgear
201 Nasal cradle
202 Right portion of nasal cradle
204 Left portion of nasal cradle
220 Support pad
222 Right portion of support pad
224 Left portion of support pad
235 Connecting member
f1 Force
f2 Force
f3 Force
$f_c$ Force
V1 First vector
V2 Second vector
X Axis
300 Nasal cushion
305 Connecting member
312 Non-face-contacting side
314 Face-contacting side
319 Aperture
320 Fluid chamber
321 Channel
322 Non-seal side portion of chamber
324 Seal-side portion of chamber
332 First inner wall portion
334 Second inner wall portion
342 First outer wall portion
344 Second outer wall portion
360 Arrows
400 Nasal cradle
402 Right portion of nasal cradle
404 Left portion of nasal cradle
420 Elastic member
422 Right side of elastic member
424 Left side of elastic member
426 Middle portion of elastic member
432 Spring
434 Spring
440 Frame
443 Engaging portion
450 Headgear
460 Supply tube
462 Inlet
502 Nasal pillow
504 Nasal pillow
512 Conical portion
514 Conical portion
520 Support member
522 Stem portion
524 Stem portion

What is claimed is:

1. A patient interface system for delivering pressurized gas to a patient's airways for treatment of sleep disordered breathing, the system comprising:
   a supply tube to deliver a supply of pressurized gas;
   a patient interface configured to receive the supply of pressurized gas from the supply tube and deliver the pressurized gas to the patient's airways, the patient interface including left and right portions configured to form a seal with the patient's face; and
   a seal maintenance device including:
      first and second arms each including upper portions disposed respectively adjacent the left and right portions of the patient interface,
      wherein, in use, the first and second arms are configured to move in response to movement of the supply tube by an external force such that the upper portions of the first and second arms respectively urge the left and right portions of the patient interface toward the patient's face to maintain the seal with the patient's face, and
      wherein the first and second arms are pivotally coupled to one another.

2. The system of claim 1, wherein the seal maintenance device further includes an actuator connected to the supply tube.

3. The system of claim 2, wherein each of the first and second arms includes lower portions connected to the actuator.

4. The system of claim 3, wherein the movement of the supply tube is configured to cause displacement of the actuator.

5. The system of claim 4, wherein the first and second arms are configured to pivot with respect to one another in response to the displacement of the actuator such that the upper portions of the first and second arms respectively urge the left and right portions of the patient interface toward the patient's face.

6. The system of claim 2, wherein the seal maintenance device further comprises an extensible connector connected to the actuator and disposed between the actuator and the patient interface.

7. The system of claim 6, wherein the extensible connector fluidly connects the supply tube and the patient interface.

8. The system of claim 6, wherein the extensible connector is configured to elongate in response to the movement of the supply tube such that the movement of the supply tube is decoupled from the patient interface.

9. The system of claim 2, wherein the actuator includes a pair of slots.

10. The system of claim 9, wherein each of the first and second arms includes lower portions connected to the actuator, and wherein the lower portions of the first and second arms are respectively slidably disposed in the slots.

11. The system of claim 1, wherein each upper portion of the first and second arms is configured to be pivotably connected to the patient interface.

12. The system of claim 1, wherein each of the first and second arms is connected to a support member, the support member being connected to a portion of a headgear.

13. The system of claim 1, wherein the seal maintenance device further includes an actuator connected to the supply tube,
wherein each of the first and second arms includes lower portions connected to the actuator,
wherein the movement of the supply tube is configured to cause displacement of the actuator,
wherein the first and second arms are configured to pivot with respect to one another in response to the displacement of the actuator such that the upper portions of the first and second arms respectively urge the left and right portions of the patient interface toward the patient's face,
wherein the seal maintenance device further comprises an extensible connector connected to the actuator and disposed between the actuator and the patient interface,
wherein the extensible connector fluidly connects the supply tube and the patient interface, and
wherein the extensible connector is configured to elongate in response to the movement of the supply tube such that the movement of the supply tube is decoupled from the patient interface.

14. A patient interface system for delivering pressurized gas to a patient's airways for treatment of sleep disordered breathing, the system comprising:
a supply tube to deliver a supply of pressurized gas;
a patient interface configured to receive the supply of pressurized gas from the supply tube and deliver the pressurized gas to the patient's airways, the patient interface including left and right portions configured to form a seal with the patient's face; and
a seal maintenance device including:
an actuator connected to the supply tube, the actuator including a pair of slots;
first and second arms each including upper portions disposed respectively adjacent the left and right portions of the patient interface; and
an extensible connector connected to the actuator and disposed between the actuator and the patient interface, the extensible connector fluidly connecting the supply tube and the patient interface,
wherein, in use, the extensible connector is configured to elongate in response to movement of the supply tube by an external force such that the movement of the supply tube is decoupled from the patient interface,
wherein the actuator is configured to be displaced in response to the movement of the supply tube, the first and second arms being configured to move relative to the patient interface in response to the displacement of the actuator such that the upper portions of the first and second arms respectively urge the left and right portions of the patient interface toward the patient's face to maintain the seal with the patient's face, and
wherein each of the first and second arms includes lower portions connected to the actuator, the lower portions of the first and second arms being respectively slidably disposed in the slots.

15. The system of claim 14, wherein, in use, the extensible connector is configured to extend its length so as to be movable from a compressed position to an extended position.

16. The system of claim 15, wherein the extensible connector is configured to retract to the compressed position when the external force is no longer applied.

17. The system of claim 14, further comprising a support member connected to a portion of a headgear, wherein a first end portion of the extensible connector is connected to the support member.

18. The system of claim 17, wherein each of the first and second arms is connected to the support member.

* * * * *